United States Patent [19]

Proksch et al.

[11] 4,224,229

[45] Sep. 23, 1980

[54] COMPOUND USEFUL IN CHOLESTEROL ASSAY PROCEDURES

[76] Inventors: Gary J. Proksch, 1045 W. 77 S. Dr.; Dean P. Bonderman, 586 W. 77th N. Dr., both of Indianapolis, Ind. 46260

[21] Appl. No.: 953,449

[22] Filed: Oct. 23, 1978

Related U.S. Application Data

[62] Division of Ser. No. 825,202, Aug. 17, 1977.

[51] Int. Cl.² .............................................. C07J 9/00
[52] U.S. Cl. .............................. 260/397.2; 260/397.5
[58] Field of Search ............... 260/397.2, 397.4, 397.5

[56] References Cited
FOREIGN PATENT DOCUMENTS 938937 10/1963 United Kingdom .................. 260/397.2

*Primary Examiner*—Elbert L. Roberts
*Attorney, Agent, or Firm*—Woodard, Weikart, Emhardt & Naughton

[57] ABSTRACT

A compound is disclosed herein which is water soluble and is useful in assay procedures for measuring serum cholesterol. In one embodiment, the compound comprises a cholesterol ester having the general formula $R_1$—$R_2$—[Cholesterol Base], in which $R_1$ is a water soluble, nonionic surfactant and $R_2$ is a dicarboxyl group bonded by ester linkages to $R_1$ and to the cholesterol. In an alternate embodiment the compound comprises a pregnenolone derivative having the general formula $R_3$—[Pregnenolone Base]—$R_4$. A compound in accordance with the present invention is useful by itself or in combination with blood serum as a standard or reference material for cholesterol assay procedues.

11 Claims, No Drawings

COMPOUND USEFUL IN CHOLESTEROL ASSAY PROCEDURES

This is a division of application Ser. No. 825,202, filed Aug. 17, 1977.

BACKGROUND OF THE INVENTION

1. Field of the Invention

The present invention relates to standards useful in assaying for cholesterol concentrations, and to the preparation thereof.

2. Description of the Prior Art

The use of serum standards or references in biochemistry analysis is well known. It is frequently advantageous, for example, to determine the level of certain constituents in the blood of a patient as a diagnostic aid. Serum standards are used in analytic procedures to provide a reference to which the patient's serum may be compared. Serum standards therefore may be required to have varying concentrations to certain components. For convenience, serum standards are commonly stored as a dry powder after lyophilization to be reconstituted at the time of use, or they are frozen and subsequently thawed for use. It is desirable that the serum standard be stable and have substantial optical clarity to minimize interference with the analytical measurement of serum constituents.

The prior art is believed to be best set forth in U.S. Pat. No. 3,853,465, issued to Rush et al. on Dec. 10, 1974, which is hereby incorporated by reference. This patent generally sets forth the facts of difficulties in photometric analysis which result from turbidity in serum and plasma samples. This is believed to be due primarily to the presence in the serum standard of certain serum proteins, particularly the low-density, triglyceride-rich lipoproteins. The problem of turbidity correspondingly increases when a serum standard is required to have increased triglyceride or cholesterol levels due to the consequent increase in the concentration of the turbiditycausing components.

The solution to the turbidity problem which Rush et al. set forth has generally been to add a surfactant to the serum or plasma to reduce the turbidity. Rush et al. disclose a surfactant of polyoxyethylated lauric acid having from 9 to 20 ethoxy groups. Compounds of this general class which have from 10 to about 20 ethoxy groups are disclosed in U.S. Pat. No. 3,260,648, issued to Fox on July 12, 1966, for use as an emulsifier for cholesterol in serum. This latter patent sets forth the use of a lower alkylphenoxypolyethoxyethanol having from about 10 to 20 ethoxy groups. While the use of such surfactants does result in a reduction in the turbidity of the serum, the products produced thereby tend to be metastable and separate after a period of time. Additionally, large amounts of surfactant are generally required and the use of such large amounts of surfactant may interfere with biological assays of serum ingredients. Moreover, even with the surfactants of this type, reconstitution of lyophilized serum having elevated cholesterol levels produces significant, measureable turbidity notwithstanding the use of the surfactant.

Aside from the problem of turbidity, it is recognized, as mentioned previously, that it is sometimes desirable to have a serum standard which has increased levels of triglycerides or cholesterol. In U.S. Pat. No. 3,764,556, issued to Kuchmak et al. on Oct. 9, 1973, there is disclosed a procedure for obtaining a cholesterol-rich protein fraction from outdated human plasma. The use of this protein fraction, however, entails several disadvantages. First, there are certain dangers involved in that the procedure by which the cholesterol-rich fraction is obtained will also result in collection and concentration of any hepatitis virus which may be present in the plasma. Additionally, it has been found that substantial serum turbidity will result upon lyophilization and reconstitution of such a prepared cholesterol standard. Also, a process which utilizes human blood as a source of cholesterol to be added in preparing a serum standard will generally be expensive.

In an article entitled "Steroid-Protein Conjugates," by Erlanger et al., Journal of Biological Chemistry, Volume 228, September, 1957, there is disclosed the preparation of water soluble conjugates of bovine serum albumin with testosterone and with cortisone. The steroids are linked by amide bonds to the lysine residues of the albumin. The conjugates disclosed in the Erlanger et al. article were proposed as antigenic compounds which could elicit antibodies having antihormonal properties. These conjugates were proposed to be useful in enabling the development and study of antihormonal principles.

SUMMARY OF THE INVENTION

One embodiment of the present invention is a compound useful in assay procedures for measuring serum cholesterol which comprises an ester of cholesterol having the formula

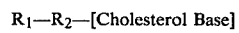

$R_1$—$R_2$—[Cholesterol Base]

in which $R_1$ is a water soluble, nonionic surfactant, and $R_2$ is a dicarboxyl group bonded by ester linkages to $R_1$ and to the Cholesterol Base, $R_1$ and $R_2$ together having a molecular weight of from about 200 to about 3000. In an alternate embodiment the compound comprises a pregnenolone derivative having the general formula $R_3$—[Pregnenolone Base]—$R_4$, $R_3$ being a hydrogen or a carboxyl group having from one to about 17 carbons, $R_4$ being selected from the group consisting of $$-\overset{CH_3}{\underset{|}{C}H}-O-\overset{O}{\underset{\|}{C}}-R_5-\overset{O}{\underset{\|}{C}}-R_6 \text{ and}$$

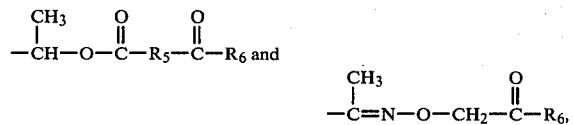

$$-\overset{CH_3}{\underset{|}{C}}=N-O-CH_2-\overset{O}{\underset{\|}{C}}-R_6,$$

$R_5$ being an alkane having from about 1 to about 8 carbons and $R_6$ being chloride or serum albumin. In other embodiments of the present invention, a compound of the described type is combined with serum or is used to reconstitute lyophilized serum to provide a standard or reference material useful in cholesteral assay procedures.

It is an object of the present invention to provide a stable and easily prepared compound useful in assay procedures for measuring serum cholesterol.

Another object of the present invention is to provide a method for producing the above-described compound.

It is a further object of the present invention to provide a compound of the described type which does not display turbidity upon lyophilization and reconstitution.

Another object of the present invention is to provide a substantially human serum which measures in assay procedures as having normal or elevated cholesterol levels, and which does not display significant turbidity upon lyophilization and reconstitution.

It is a further object of the present invention to provide a method for preparing a substantially human serum which is useful as a standard or reference material and which fulfills the above-described objectives.

Another object of the present invention is to provide a compound which combined with serum produces a standard or reference material useful in cholesterol assay procedures.

It is another object of the present invention to provide a compound useful as a diluent for lyophilized serum to produce a cholesterol standard.

Further objects and advantages of the present invention will be apparent from the description of the preferred embodiments which follows.

DESCRIPTION OF THE PREFERRED EMBODIMENTS

Standard or reference materials are generally required in the performance of assay procedures directed toward determining the levels of cholesterol in serum or plasma. In order to retain the reference material for use over a period of time it is desirable to store the material either in the frozen or lyophilized state. The material is subsequently thawed or reconstituted with aqueous media for use. As previously noted, however, standard or reference materials heretofore have displayed significant turbidity, especially upon thawing or reconstitution. This turbidity interferes with the use of standard colorimimetric or turbidimetric measuring devices. It is therefore highly desirable to provide a standard or reference material which may be stored in the frozen or lyophilized state, but which does not display turbidity when thawed or reconstituted for use.

Human serum or plasma contains four major classes of lipoproteins. Lipoproteins are a complex of a protein with a lipid, and the four major classes are chylomicrons, very low density lipoproteins (pre-beta lipoproteins), low density lipoproteins (beta lipoproteins) and high density lipoproteins (alpha lipoproteins). The actual proportions of the various classes of lipoproteins present in a serum or plasma sample vary with respect to certain physical and chemical parameters. However, the alpha lipoproteins generally comprise between 20% and 40% of the lipoprotein content of human serum or plasma. Most of the serum cholesterol is associated with the beta lipoproteins.

The problem associated with the lipoproteins is that their presence in serum tends to result in turbidity in the serum, particularly upon thawing or reconstitution of a stored standard or reference material. It is believed that the turbidity is a result particularly of the presence of the lower density lipoproteins. As a result, standards or reference materials used in assay procedures for measuring serum cholesterol generally become turbid because of the presence of the lipoproteins. Various techniques have been employed to attempt to reduce the turbidity of the thawed or reconstituted serum standards. The present invention provides a new and useful compound which may be applied in various manners to produce a standard or reference material which is useful in assay procedures for measuring serum cholesterol. The compound of the present invention further does not become turbid upon freezing and thawing, or upon lyophilization and reconstitution with an aqueous media.

In accordance with one embodiment of the present invention, a compound is provided which is useful in assay procedures for measuring serum cholesterol and which comprises an ester of cholesterol having the general formula:

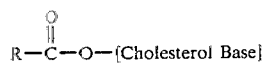

in which R is a water soluble, nonionic surfactant having a molecular weight of from about 200 to about 3000. The attachment to the Cholesterol Base is at the 3 beta position of the Cholesterol Base. More preferably, R has a molecular weight of from about 300 to about 1000, and contains between about 4 and about 20 carbon atoms. R should be relatively inert, preferably containing several ethoxy groups, and more specifically comprising polyethoxyethanyl. The term "Cholesterol Base" is defined as the entire portion of the cholesterol molecule except for the hydroxyl group normally attached at the 3 beta position, the term "Cholesterol Base" thus being equivalent to the material known by conventional steroid nomenclature as cholest-5-en.

In a related embodiment of the present invention, the compound is represented by the general formula:

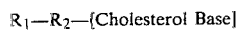

in which $R_1$ is a water soluble, nonionic surfactant, and $R_2$ is a dicarboxyl group bonded by ester linkages to $R_1$ and to the Cholesterol Base. The $R_2$ group is attached at the 3 beta position of the Cholesterol Base. $R_1$ and $R_2$ together shouuld have a molecular weight of from about 200 to about 3000, and more preferably have a combined molecular weight of from about 300 to about 1000. $R_1$ and $R_2$ preferably have a total of between about 5 to about 21 carbon atoms, with $R_2$ preferably having between about 3 and about 8 carbon atoms. $R_1$ should be relatively inert or non-reactive to be useful with common assay procedures, and $R_1$ preferably includes several ethoxy groups. A particular compound of the described class which has been found to be well suited for use in conjunction with cholesterol assay procedures is one in which $R_1$ comprises polyethoxyethanyl and $R_2$ is an adipyl group.

Compounds of the above-described classes may be readily produced in accordance with known, chemical synthesis techniques. In the preferred method for forming the above-described compounds, cholesterol is reacted with a dicarboxyl compound to bond the cholesterol to one of the carboxyl groups and to thereby form a cholesterol ester. The ester is then coupled to a nonionic surfactant, such as polyethoxyethanol, to form the final compound. The dicarboxyl compound preferably has betwen about 3 and about 8 carbon atoms, and the surfactant preferably has a molecular weight of from about 300 to about 1000. It has been found that a particularly preferred embodiment of the present invention is produced by bonding the cholesterol to an adipyl compound, which is in turn bonded to a surfactant containing several ethoxy groups and having from about 4 to about 20 carbon atoms.

The classes of compounds of the present invention are applied in various manners to provide a standard or reference material useful in cholesterol assay procedures. An aqueous solution of the water-soluble, cholesterol compound of the present invention is used as a standard or reference material. The cholesterol compound of the present invention is utilized to prepare an aqueous solution which will measure as having cholesterol in the concentration of a preselected value, such as that corresponding to a normal or elevated level of cholesterol in human serum or plasma. The water-soluble, cholesterol compounds of the present invention are also combined with human or other serums to provide a standard or reference material. The serums with which the cholesterol compounds are combined include, for example, serum containing essentially all normal human serum components; serum having essentially all of its normally present pre-beta lipoproteins, beta lipoproteins, and chylomicrons removed; and, serum having normally present lipoproteins and chylomicrons removed. Removal of the lower density lipoproteins from the serum with which the cholesterol compounds are combined is advantageous in that it further reduces the possibility of turbidity upon freezing and thawing, or upon lyophilization and reconstitution with aqueous media. Removal of all of the lipoproteins is advantageous in that the selective removal of only the lower density lipoproteins is not involved. In a further application of the present invention, aqueous solutions of the cholesterol compounds are combined with lyophilized serum which may, for example, be one of the three types of serum previously described. Any of the standards or reference materials of the present invention may be frozen or lyophilized for storage, and upon thawing or reconstitution with aqueous media, do not display significant turbidity.

The cholesterol compounds of the present invention in certain embodiments are combined with blood plasma or serum, as previously described. These embodiments utilize blood plasma, which is defined as the liquid part of the blood containing fibrinogen. Normal human plasma is obtained from pooled blood. The pooled blood includes approximately equal volumes of the liquid portions of whole blood from not less than 8 adult humans. Outdated, citrated whole blood, which is old whole blood to which citrate, phosphate, and dextrose have been added, is preferable in view of its low cost. The normal human serum is derived from the pooled blood plasma. The serum is the clear, amber, alkaline fluid of the blood from which cellular elements have been removed by clotting. The serum contains the salts, soluble protein and lipoproteins. The lipoproteins are rich in triglycerides and cholesterol.

As outlined previously, in one embodiment of the invention a cholesterol compound of the described classes is added to the human serum. The preferred compound is polyethoxyethanylcholesteryl-adipate, although other compounds of the described classes may similarly be used. In another embodiment of the invention, the human serum is processed to remove certain constituents prior to the addition of the cholesterol compound. Preferably, these constituents which have been found to contribute to turbidity of the reconstituted serum are removed, as is disclosed in U.S. Pat. No. 3,955,925, issued to Proksch and Bonderman on May 11, 1976, the relevant parts of which are hereby incorporated by reference. The cholesterol compound, such as the polyethoxyethanyl-cholesteryl-adipate, is added to achieve the desired cholesterol-measuring concentration. The resultant serum standard is stable and displays good optical clarity upon reconstitution from the lyophilized state.

Another aspect of this invention involves the addition of the cholesterol compound to animal serum, such as horse or bovine serum, to obtain desired cholesterol concentrations. The resulting serum is stable in lyophilized form and readily reconstitutes to an optically clear serum.

In still another embodiment of the present invention, the cholesterol compounds are added as diluents to lyophilized human or animal serum to produce an optically clear and stable standard. The lyophilized human or animal serum have normal or reduced levels of lipids, triglyceride, or cholesterol. The cholesterol compounds are added to the lyophilized serum as aqueous solutions. The concentration of the lipids, triglyceride and cholesterol in the resulting serum standards or references are controlled by the concentration of the cholesterol compound in the aqueous diluent, and by the amount of diluent added to the lyophilized serum.

In an alternate embodiment the compound is represented by the general formula:

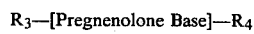

$R_3$ is attached at the 3 beta position of the Pregnenolone Base and is a hydroxyl group or an ester group preferably having from about one to about 17 carbon atoms. $R_4$ is attached at the 17 position of the Pregnenolone Base and is selected from the group consisting of

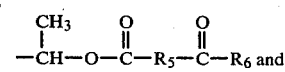

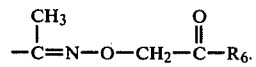

$R_5$ is an alkane preferably having from about one to about 8 carbon atoms. $R_6$ is either a chloride atom or is serum albumin, such as bovine serum albumin for example, attached by amide bonds with its lysine residues. The term "Pregnenolone Base" is defined as the entire portion of the pregnenolone molecule except for the hydroxyl group normally attached at the 3 beta position and also except for the normally present 20 methyl keto group, the term "Pregnenolone Base" thus being equivalent to the material known under conventional steroid nomenclature as Δ5-androsten. The above described pregnenolone derivatives are useful in the same fashion as the previously described cholesterol derivatives.

Production of the above-described pregnenolone derivatives is readily accomplished by known chemical synthesis techniques. In one procedure a carboxylic acid is attached to the 3 beta position of the pregnenolone to block that position from interfering with the intended reactions in subsequent steps. The resulting product is then combined with sodium borohydride to provide a hydroxyl group at the 20 keto position which is subsequently reacted with a diacid chloride or with a dicarboxylic acid and isobutyl chlorocarbonate to yield the desired product. This end product may further be combined with serum albumin to form an alternate compound in accordance with the present invention.

In another procedure the pregnenolone is reacted, for example with a carboxylic acid, to provide an ester at the 3 beta position. The resulting product is reacted with carboxymethoxylamine hemihydrochloride to produce the desired final product. This final product may additionally be combined with bovine serum albumin to form another form of compound in accordance with the present invention.

In a second alternate embodiment, the compound of the present invention comprises a cholesterol derivative having the general formula $R_7$—$R_8$—[Cholesterol Base] in which $R_7$ is serum albumin and $R_8$ is a dicarboxyl group. $R_8$ is bonded by an ester linkage to the Cholesterol Base at the 3 beta position, and is attached to $R_7$ by amide bonds with the lysine residues of the serum albumin. $R_8$ preferably has between about 1 and about 20 carbon atoms and more preferably between about 3 and about 8 carbon atoms. This second alternate embodiment is useful in like fashion as the previously described embodiments.

The following examples more fully illustrate the preferred embodiments of the present invention.

EXAMPLE 1

A cholesterol ester of the class constituting the preferred embodiment of the present invention was prepared by the following procedure. To 150 ml of dry toluene was added 11.6 [0.03 moles] of cholesterol, and 7.6 g [0.04 moles] of adipyl dichloride was added thereto. The mixture was incubated at 35° C. under a 5 mm of mercury vacuum for 60 minutes to form cholesteryl-adipate.

A solution of polyethylene glycol, having an average molecular weight of 600, was separately prepared by adding 36 g [0.06 moles] of carbowax to 75 ml of toluene. The particular carbowax solution utilized is available under the trademark PEG-600. The polyethylene glycol preparation was then added to the cholesteryl-adipate mixture.

The resultant mixture was stirred for 45 minutes and then extracted three times with an equal volume of water at 80° C. to remove the water-soluble impurities. The aqueous extracts were discarded. The toluene was then removed by evaporation at 80° C. The resultant material was cooled to 70° C. and was then suspended in 100 ml of methanol. After stirring for 60 minutes, the methanol-insoluble residue was removed by filtration, and the methanol was subsequently removed by evaporation. The resultant viscous liquid was then twice extracted with 100 ml of petroleum ether having a boiling point range of 30°-60° C., and the viscous liquid was placed in a vacuum oven at 50°-60° C. until the final traces of solvent were removed.

About 10.5 g of polyethoxyethanyl-cholesteryl-adipate (PCA) were obtained. The viscous PCA normally contained about 300 mg of cholesterol per gram. Analysis of the PCA by chromatographic techniques using acetone as the solvent indicated that the preparation consisted of a series of cholesterol-containing molecules having a mobility less than cholesterol. Although the preparation did not represent a single unimolecular species, but a series of homologous derivatives, the PCA was found to be useful without further treatment as a water-soluble, cholesterol additive for preparing standard and reference materials.

Aqueous solutions of the PCA prepared by the above method were prepared to provide assay standards of various cholesterol concentrations and were measured for their cholesterol activity, which as previously mentioned was found to correspond to about 300 mg of cholesterol per gram. Various amounts of water were then added to samples of the PCA preparation to produce solutions with the various levels of cholesterol. These standards were found to measure accurately in cholesterol assay procedures, and remained stable for 6 months at 5° C. The cholesterol standards produced in this manner, when stored either in the frozen or lyophilized condition for extended periods of time, did not show a significant effect on the measured value of the cholesterol in the standard.

EXAMPLE 2

A variety of cholesterol esters were prepared by the method of Example 1, except that different dicarboxyl groups were used. Dicarboxyl groups containing from 4 to 7 carbon atoms were used to produce the succinate, glutarate, adipate and pimelate forms of the polyethoxyethanyl-cholesteryl compounds. Each of the compounds measured accurately in cholesterol assay procedures, although the succinate form did not measure as accurately as the others. These preparations also remained stable upon storage for 6 months at 5° C.

EXAMPLE 3

Cholesterol esters were prepared in accordance with the methods of Examples 1 and 2, with the exception that the following surfactants were used: polyethoxyethanyl having average molecular weights of 80, 150, 850 and 2800, and polyoxypropylene having an average molecular weight of 500. The prepared compounds were found to measure well in cholesterol assay procedures and remained stable upon storage for extended periods of time.

For any preparation of a cholesterol ester in accordance with the procedure of Examples 1-3 and others it was found that the cholesterol activity of the ester should be assayed to standardize the compound for use. Water is then added to produce a solution of the ester having the desired level of cholesterol. Alternatively, the ester was stored in the concentrated form, and was subsequently diluted for use.

EXAMPLE 4

A normal 1000 ml pooled human blood plasma sample was obtained and converted to serum by clotting. Cholesterol esters prepared in accordance with the methods of Examples 1-3 were added to samples of the serum to bring the cholesterol content to desired levels. The resultant, substantially human serums provided excellent serum standards for elevated cholesterol levels and displayed excellent optical clarity. Portions of the prepared serums were stored for six months by freezing and by lyophilizing, and upon thawing or reconstitution with water, respectively, were optically clear.

EXAMPLE 5

The procedures of Example 4 were followed exactly except that the human serum was first processed to remove the beta lipoproteins, pre-beta lipoproteins and chylomicrons. The processing of the human serum was performed by the method disclosed in U.S. Pat. No. 3,955,925, issued to Proksch and Bonderman on May 11, 1976, the pertinent portions of which are hereby incorporated by reference. The resultant, substantially human serums provided excellent serum standards which measured accurately for normal and elevated levels of cholesterol and which displayed excellent optical clarity. The serum preparations remained stable upon storing for 6 months in the lyophilized or frozen state, and were optically clear upon use.

EXAMPLE 6

The procedures of Example 4 were followed exactly except that the human serum was first processed to remove the normally present alpha lipoproteins, beta lipoprotens, pre-beta lipoproteins and chylomicrons. The processing of the human serum was performed by the technique of Jonas as described in the Journal of Biological Chemistry, Volume 247, pages 7767 et seq. Briefly, the serum was allowed to clot at room temperature and was centrifuged at 60,000 rpm for about 24 hours. A first fraction of primarily low density lipoproteins and chylomicrons was then removed and discarded. The remaining solution was centrifuged under the same conditions and a second fraction comprising primarily high density lipoproteins was drawn off the top and discarded. The cholesterol esters were then added in aqueous solution to portions of the processed human serum as previously described.

The resultant substantially human serums provided excellent serum standards which measured accurately for normal and elevated levels of cholesterol. The serum standards displayed excellent optical clarity both originally and after storage for 6 months in either the lyophilized or frozen state.

EXAMPLE 7

The procedures of Examples 5 and 6 were followed exactly except that the human serum was processed by the method of Oncley et al. as disclosed in the Journal of the American Chemical Society, Volume 79, pages 4666 et seq. Briefly, a solution of dextran sulfate solution was added with stirring to the serum. A lipoprotein-dextran sulfate precipitate containing the lipoproteins was allowed to form and was separated by centrifugation. Portions of the processed serum were then diluted with aqueous solutions of the cholesterol esters to provide standards with the desired levels of cholesterol. The resulting substantially human serums provided cholesterol serum standards which measured accurately and which displayed excellent optical clarity initially and upon storage in the lyophilized or frozen state.

EXAMPLE 8

Substantially human serum standards were prepared by procedures similar to those in Examples 5–7, except that the cholesterol esters were added as diluents to lyophilized forms of the processed human serums. The human serum was processed in accordance with the procedures detailed in Examples 5–7. The processed serums were then lyophilized. Diluents comprising aqueous solutions of desired concentrations of the cholesterol esters were then added in desired amounts to portions of the lyophilized, processed human serums. The resultant, substantially human serums displayed excellent optical clarity and measured well as cholesterol standards, even when the human serum was stored in the lyophilized form for 6 months before dilution with the cholesterol ester solutions.

EXAMPLE 9

The procedures of Examples 5–8 were followed exactly except that bovine and horse serums were used. Again, excellent serum standards were obtained which were stable, measured accurately in cholesterol assay procedures, and displayed excellent optical clarity initially and upon storage.

EXAMPLE 10

A solution was prepared by combining 1.08 g of pregnenolone and 1.07 g of carboxymethoxylamine hemihydrochloride in 200 ml of ethanol. This solution was made alkaline by adding 20 ml of 5% NaOH, and the resulting solution was refluxed for one and a half hours. The refluxed solution was diluted with water and extracted with ether. The aqueous phase was acidified with hydrochloric acid and the resulting precipitate was extracted with ether. The ether extract was washed with water and dried. The resultant product comprised pregnenolone 20-carboxymethoxyloxime and was soluble in a basic aqueous solution. The product measured as cholesterol in standard assay procedures and was not turbid upon lyophilization and reconstitution with aqueous media.

EXAMPLE 11

A solution was prepared by combining 1.2 g of pregnenolone 20-carboxymethoxyloxime prepared in accordance with Example 10 and 0.80 ml of tri-n-butylamine in 30 ml of dioxane and the solution was cooled to 10° C. Added to the cooled solution was 0.40 ml of isobutyl chlorocarbonate and the resulting reaction was allowed to proceed at 4° C. for 20 minutes. The mixture was added to a stirred, cooled solution of 4.2 g of bovine serum albumin in 220 ml of an equal mixture of water and dioxane and 4.2 ml 1 N NaOH. An additional 2.0 ml of 1 N NaOH was added after one hour and the mixture was continued to be stirred and cooled for an additional three hours.

The solution was dialyzed against running water for 18 hours and hydrochloric acid was added in an amount sufficient to achieve a pH of 4.5. The product precipitated and was collected by centrifugation after storage for 4 days. The precipitate comprised a conjugate of the pregnenolone 20-carboxymethoxyloxime and bovine serum albumin joined together by amine bonds. The product was soluble in water and measured as cholesterol in assay procedures. The product was stable and did not produce a turbid solution upon lyophilization and reconstitution with aqueous media.

EXAMPLE 12

A solution was prepared by adding 5.2 g of pregnenolone laurate to 200 ml isopropyl alcohol and to this solution was added 0.125 g sodium borohydride (NaBH$_4$). The resulting mixture was allowed to stand at room temperature at two days and was then combined with 40 ml of water. A precipitate resulted and was recrystalized from 100 ml of 80% ethanol and water. The recrystalized precipitate comprised pregnene-20-ol-3-beta laurate, hereinafter referred to as the first precipitate. A solution was prepared by adding 5.2 g of the first precipitate to 100 ml of the dioxane and added to this solution were 1.55 g of succinyl chloride and 1.1 g of triethylamine. The resulting solution was added in one portion to 12 g of bovine serum albumin disolved in 100 ml of one to one dioxane and water and 5 ml of 1 N soduim hydroxide to achieve a pH of 8–10. The resulting solution was purified by dialyzing for 24 hours against distilled water and the solution was then acidified and the resulting precipitate removed by centrifugation.

EXAMPLE 13

A solution was prepared by adding 5.2 g of the first precipitate prepared in accordance with example 12, together with 1.5 g of succinyl chloride and 1.01 g of triethylamine, to 100 ml of toluene. The resulting solution was warmed to 40° C. and maintained at that temperature for 1½ hours. The warmed solution was added in one portion to a second solution comprising 15 g of polyethylene glycol (having an average molecular weight of 1000) and 1.01 g triethylamine dissolved in 100 ml of toluene. The resulting mixture was maintained for 1½ hours at 40° C. and was extracted with 100 ml of 80% saturated sodium chloride solution, the sodium chloride solution then being discarded. The toluene was then removed from the resulting mixture by evaporation and the product was dissolved in 20 ml of acetone, and 1 ml of water was added. The acetone solution was then extracted twice with 50 ml of hexane, and the hexane was then discarded. The acetone was removed by evaporation and the product thereby obtained comprised 3-beta laurate pregnene-20-succinyl polyethylene glycol. The product was found to be soluble in water and to measure as cholesterol in common assay procedures.

EXAMPLE 14

The procedures of Examples 12 and 13 were repeated using pregnenolone acetate and pregnenolone palmitate instead of the pregnenolone laurate, and products displaying similar results are obtained.

EXAMPLE 15

The procedures of Examples 12-14 were repeated using sebacyl chloride and adipyl chloride instead of the succinyl chloride and products displaying similar results were obtained.

EXAMPLE 16

A solution was prepared by adding 4.29 g of cholesterol hemisuccinate to 50 ml of dioxane and to that solution was added 1 g of triethylamine. To the resulting solution was added 1.37 g of isobutyl chlorocarbonate and the resulting mixture was warmed gently for 20 minutes. The warmed solution was then added to a second solution comprising 12 g of bovine serum albumin added to 500 ml of one to one dioxane in water and 5 ml of 1 N sodium hydroxide. The solution was stirred and cooled for an hour and was then purified by dialyzing against distilled water as described in example 12. Hydrochloric acid was then added to the solution to achieve a pH of about 4.5 and the resulting precipitate was collected by centrifugation. The precipitated product comprised a conjugate of the cholesterol and the bovine serum albumin with a dicarboxyl group having a first carboxyl group attached at the 3 beta position of the cholesterol and further having a second carboxyl attached by amide bonds to one of the lysine residues of the bovine serum albumin. The product was found to be soluble in water and measured as cholesterol in normal assay procedures.

EXAMPLE 17

The procedure of Example 16 was repeated using cholesterol hemisebacylate and cholesterol hemiadipate instead of the cholesterol hemisuccinate and products yielding similar results were obtained.

EXAMPLE 18

Performance of the procedures of Examples 12 and 14-17 using horse serum albumin, human serum albumin and bovine serum albumin yielded products displaying similar results.

What is claimed is:

1. A compound useful in assay procedures for measuring serum cholesterol comprising a pregnenolone derivative having the formula:

in which:

$R_3$ is attached at the 3 beta position of the Pregnenolone Base and is a compound selected from the group consisting of a hydroxyl group and an ester group having from about 2 to about 17 carbon atoms; and $R_4$ is attached at the 17 position of the Pregnenolone Base and is a compound selected from the group consisting of

 and

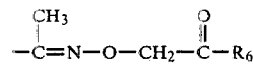

in which $R_5$ is an alkane having between 1 and about 8 carbon atoms and $R_6$ is selected from the group consisting of chloride and serum albumin.

2. The compound of claim 1 in which $R_3$ is a hydroxyl group and $R_4$ is

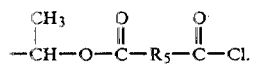

3. The compound of claim 2 in which $R_3$ is a hydroxyl group, $R_4$ is

and $R_6$ is serum albumin.

4. The compound of claim 1 in which $R_3$ is a hydroxyl group and $R_4$ is

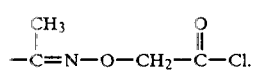

5. The compound of claim 1 in which $R_3$ is a hydroxyl group, and $R_4$ is

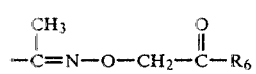

and $R_6$ is serum albumin.

6. The compound of claim 1 in which $R_3$ is an ester group, and $R_4$ is

7. The compound of claim 2 in which $R_3$ is an ester group, and $R_4$ is

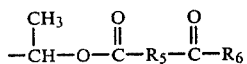

and $R_6$ is serum albumin.

8. The compound of claim 1 in which $R_3$ is an ester group, and $R_4$ is

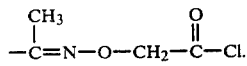

9. The compound of claim 1 in which $R_3$ is an ester group, and $R_4$ is

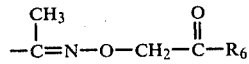

and $R_6$ is serum albumin.

10. A compound useful in assay procedures for measuring serum cholesterol comprising an ester of cholesterol having the formula:

R—7—R8—[Cholesterol Base]

in which:
  $R_7$ is serum albumin; and
  $R_8$ is a dicarboxyl group having between about 3 and about 20 carbon atoms, the dicarboxyl group having a first carboxyl group attached by an ester linkage to the 3 beta position of the Cholesterol Base and further having a second carboxyl group attached to the serum albumin by an amide bond with one of the lysine residues of the serum albumin.

11. The compound of claim 10 in which $R_8$ has between about 4 and about 10 carbon atoms.

* * * * *